United States Patent
Knox et al.

(10) Patent No.: US 7,501,236 B1
(45) Date of Patent: Mar. 10, 2009

(54) NMR SPECTROSCOPIC IN VITRO ASSAY USING HYPERPOLARIZATION

(75) Inventors: Peter Knox, Chalfont St. Giles (GB); Neil Cook, Princeton, NJ (US); Klaes Golman, Malmo (SE); Haukur Johannesson, Malmo (SE); Oksar Axelsson, Malmo (SE); Jan Henrik Ardenkjaer-Larsen, Malmo (SE)

(73) Assignee: GE Healthcare Limited, Buckinghamshire (GB)

( * ) Notice: Subject to any disclaimer, the term of this patent is extended or adjusted under 35 U.S.C. 154(b) by 0 days.

(21) Appl. No.: 09/869,629

(22) PCT Filed: Dec. 23, 1999

(86) PCT No.: PCT/GB99/04410

§ 371 (c)(1),
(2), (4) Date: Sep. 21, 2001

(87) PCT Pub. No.: WO00/40988

PCT Pub. Date: Jul. 13, 2000

(30) Foreign Application Priority Data

Dec. 30, 1998 (GB) ................................. 9828852.5
Aug. 2, 1999 (GB) ................................. 9918096.0

(51) Int. Cl.
*C12Q 1/68* (2006.01)
(52) U.S. Cl. .......................................................... 435/6
(58) Field of Classification Search .................... 435/6, 435/4, 5, 7.1–7.95, 69.1, 70.1; 422/50; 436/514–519
See application file for complete search history.

(56) References Cited

U.S. PATENT DOCUMENTS

| | | | |
|---|---|---|---|
| 5,475,304 A | 12/1995 | Prinz | |
| 5,479,925 A | 1/1996 | Dumoulin et al. | |
| 5,545,396 A | 8/1996 | Mitchell et al. | |
| 5,834,226 A * | 11/1998 | Maupin | 435/15 |
| 6,103,492 A * | 8/2000 | Yu | 435/69.1 |
| 6,110,749 A * | 8/2000 | Obremski et al. | 436/527 |
| 6,278,893 B1 * | 8/2001 | Ardenkjaer-Larson et al. | 600/420 |
| 6,426,058 B1 * | 7/2002 | Pines et al. | 424/9.3 |
| 6,574,496 B1 * | 6/2003 | Golman et al. | 600/420 |

FOREIGN PATENT DOCUMENTS

WO    WO 97 37239 A    10/1997

OTHER PUBLICATIONS

Hall et al., "Polarization-Enhanced NMR Spectroscopy of Biomolecules in Frozen Solution", Science, vol. 276, May 1997.*
Neild et al., "Uroscopy in the 21$^{st}$ Century: high-filed NMR spectroscopy", Nephrol DialTransplant (1997), 12: 404-417.*
Buck et al., "Photochemically induced dynamic nuclear polarization investigation of complex formation of the NH2-terminal DNA-binding domain of lac respressor with poly[d(AT)]", Biochemistry, vol. 77, No. 9, pp. 5145-5148.*
Katahira et al., "NMR studies of G:A mismatches in oligodeoxyribonucleotide duplexes modeled after ribozymes", Nucleic Acids Research, 1993, vol. 21, No. 23, pp. 5418-5424.*
Spooner, P. J. R., et al. "Weak Substrate Binding to Transport Proteins Studied by NMR" Biophysical Journal, Dec. 1998, vol. 75, No. 6, pp. 2794-2800.
Natterer, J., et al. "Parahydrogen Induced Polarization" Progress in Nuclear Magnetic Resonance Spectroscopy, Nov. 1997, vol. 31, No. 4, pp. 293-315. specifically: Chapter 3 "Experimental Aspects"; Chapter 5 "Applications"; and Chapter 6 "The Future".
Ardenkjaer-Larsen, J. H., et al. "EPR and DNP Properties of Certain Novel Single Electron Contrast Agents Intended for Oximetric Imaging" Journal of Magnetic Resonance, Jul. 1998, vol. 133, No. 1, pp. 1-2.
Hall, D. A., et al. "Polarization-Enhanced NMR Spectroscopy of Biomolecules in Frozen Solution" Science, May 9, 1997, vol. 276, No. 5314, pp. 930-932.

* cited by examiner

*Primary Examiner*—Ann Y. Lam
(74) *Attorney, Agent, or Firm*—Robert F. Chisholm

(57) ABSTRACT

An in vitro assay method which comprises the use of an assay reagent containing at least one NMR active nucleus, and hyperpolarising at least one NMR active nucleus of the assay reagent; and analysing the assay reagent and/or the assay by NMR spectroscopy and/or NMR imaging. The assay reagent may contain an artificially high concentration of an NMR active nucleus.

20 Claims, 2 Drawing Sheets

Spin dipole spectra

Proteolysis

2 Individual spectra

NMR SPECTROSCOPIC IN VITRO ASSAY USING HYPERPOLARIZATION

FIELD OF THE INVENTION

This invention is concerned with nuclear magnetic resonance spectroscopy. The technique involves observing the spectrum of a NMR active nuclear species, particularly a hyperpolarised nucleus, in order to obtain information about the environment in which the species is present. The spectra of NMR active nuclei vary depending on their environment, as reported in the literature (PNAS, 93, 12932-6, 1996).

BACKGROUND OF THE INVENTION

Noble gases having non-zero nuclear spin can be hyperpolarised, i.e. have their polarisation enhanced over the equilibrium polarisation, e.g. by the use of circularly polarised light. Preferred techniques for hyperpolarisation include spin exchange with an optically pumped alkali metal vapour and metastability exchange. Noble gases to which this technique can be applied include $^3$He and $^{129}$Xe. As described by M S Albert et al in U.S. Pat. No. 5,545,396, the technique can be used to prepare hyperpolarised noble gases which can then be administered by inhalation for magnetic resonance imaging of the human body.

It is known that the hyperpolarisation of a noble gas can be transferred to another NMR active species by physical contact. Thus WO 97/37239 (Lawrence Berkeley National Laboratory) describes a method which involves: contacting a sample containing an NMR active nucleus with a hyperpolarised noble gas; scanning the sample using nuclear magnetic resonance spectroscopy, magnetic resonance imaging, or both, in order to detect the NMR active nucleus. WO 98/30918 (Nycomed Imaging AS) relates to ex-vivo dynamic nuclear polarisation (DNP) of the NMR active nuclei of an MR imaging agent by a hyperpolarised gas where the gas is separated from the MR imaging agent prior to administration to the body.

The present invention concerns the hyperpolarisation of one or more NMR active nuclei of compounds involved in an assay. The hyperpolarisationmay be carried out using a variety of techniques, such as polarisation transfer from a noble gas, "Brute force", DNP (WO 98/58272, Nycomed Imaging AS) and the para hydrogen (p-H$_2$) method, as explained below.

The transfer of hyperpolarisation according to the present invention may be achieved by using a hyperpolarised noble gas, preferably $^3$He or $^{129}$Xe, or a mixture of such gases, to effect nuclear polarisation of an assay reagent comprising at least one NMR active nucleus other than the noble gas. The hyperpolarisation of the assay reagent may also be achieved by using anartificially enriched hyperpolarised noble gas, preferably $^3$He or $^{129}$Xe.

Alternatively, hyperpolarisation may be imparted to atoms of significance in biological systems (e.g. $^{13}$C, $^{15}$N, $^{31}$P, $^{29}$Si, $^{19}$F and $^1$H isotopes) by thermodynamic equilibration at very low temperature, suitably below 1K, preferably as close to 0 K as possible, and in the presence of a high magnetic field ("Brute force").

A further alternative is that hyperpolarisation may be imparted by dynamic nuclear polarisation (DNP). In the solid phase, the material is mixed with a paramagnetic species (DNP agent), for example a transition metal ion such as chromium (V) or manganese (II) and/or a free radical generator or other particles having associated free electrons. The method utilises a moderate or high magnetic field and very low temperature, e.g. by carrying out the conversion in liquid helium and a magnetic field of about 1 T or above.

A further technique for imparting hyperpolarisation is para hydrogen induced polarisation which involves cooling hydrogen to a low temperature, e.g. 20 K or less, to give para hydrogen enriched hydrogen. This enriched hydrogen is then used to hydrogenate an unsaturated target organic molecule (containing NMR active nuclei) imparting a non-thermodynamic spin configuration to the target molecule.

DETAILED DESCRIPTION OF THE PREFERRED EMBODIMENTS

Figure 1:
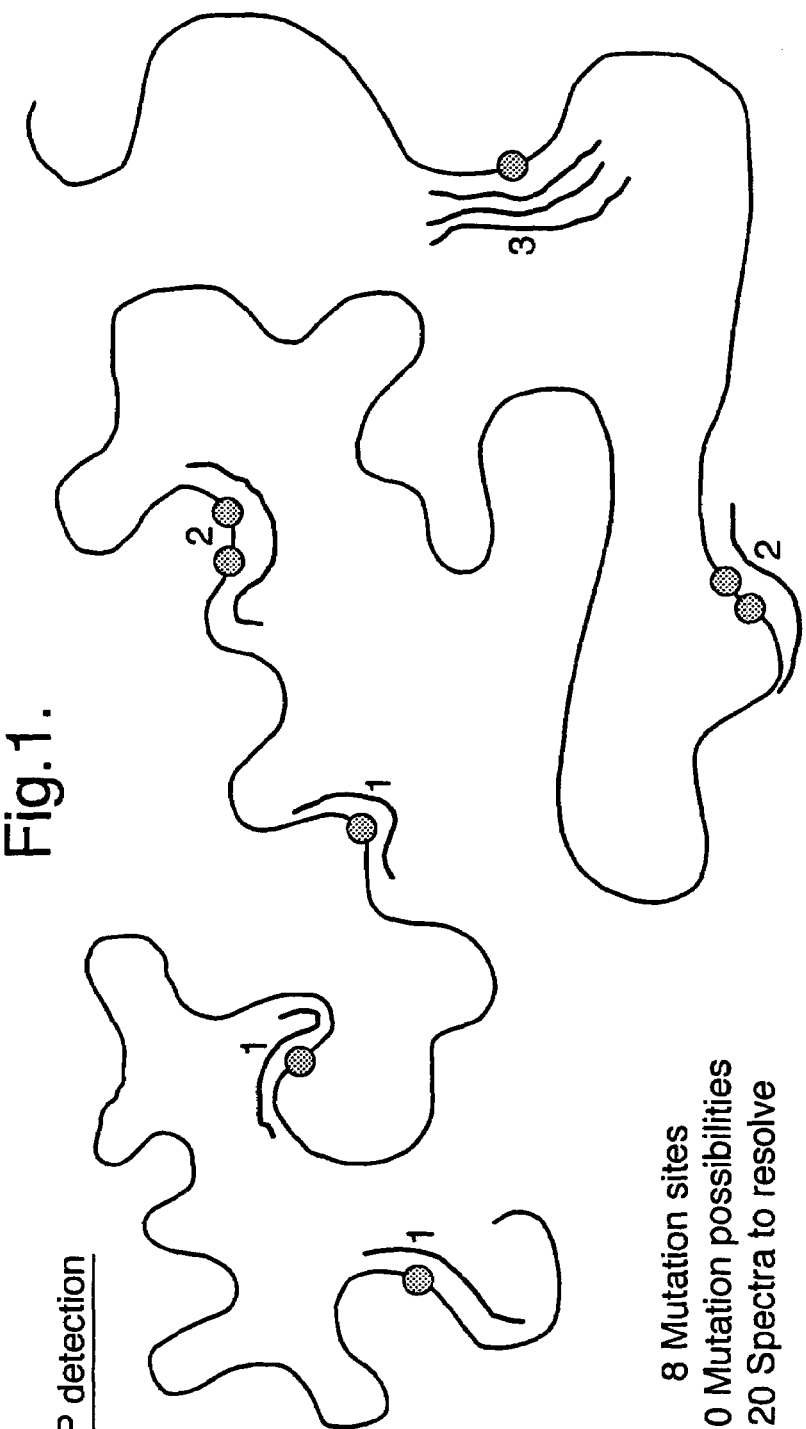
FIG. 1 is a schematic representation of a gene with oligonucleotide probes bound for the detection of the presence of a specific mutation (1), or more than one mutation using a single probe (2) or a set of probes (3).

A yet further method covered by the present invention for preparing hyperpolarised materials is spin refrigeration. With this technique, the assay reagent is doped with or intimately mixed with a suitable paramagnetic material in crystal form (e.g. crystalline powder) with a symmetry axis of order three or more. One advantage with this technique is that there is no need for a uniform magnetic field since no resonant excitation field is applied. The sample is rotated to bring the electron paramagnetic resonance into contact with the nuclear spins, which are then cooled. The rotation is repeated until the nuclear spin polarisation is steady.

The present invention can give the same information about the target compared to any previously known NMR method, but with the advantage of increased sensitivity. A further advantage of this invention is that assay reagent containing an NMR active nucleus may in many cases, provide the same information previously provided by corresponding $^{14}$C-labelled compounds, whilst being free from the problems associated with radioactive isotopes.

One further advantage according to the present invention is the increased signal-to-noise ratio. Another improvement with the present invention is that the time required to perform the assay is in general much shorter than the previously known methods. These improved parameters/results may be expressed as a "shortening effect", being the improvement of signal-to-noise ratio per unit time, and will be discussed further.

Yet another advantage compared e.g. with assays using fluorescent reagents is that there is no need to add an additional chemical component to the assay reagent to assist detection. There is always a disadvantage with techniques such as the fluorescent methods because the additional chemical component may influence the measurement.

The present invention provides an in vitro assay method which comprises:
  a) using an assay reagent containing at least one NMR active nucleus to perform an assay, and
  b) hyperpolarising at least one NMR active nucleus of the assay reagent; Wherein steps a) and b) are performed simultaneously or sequentially in either order, and c) analysing the assay reagent and/or the assay by NMR, and d) optionally using the NMR data obtained in step c) to generate further assay result(s).

As used herein, NMR active nuclei are those having non-zero nuclear spin and include $^1H$, $^{13}C$, $^{15}N$, $^{19}F$, $^{1329}Si$, $^{31}P$ and/or deuterium. Of these, $^{13}C$ and $^{15}N$ are preferred and $^{13}C$ is particularly preferred. Preferably the assay reagent for use in the assay according to this invention comprises an artificially-enriched abundance of an NMR active nucleus.

In a further preferred embodiment of the invention, the enriched compound comprises the artificially enriched NMR active nuclei, e.g. $^{13}C$, at one specific position. Alternatively, in another preferred embodiment the compound comprises enriched NMR active nuclei in 1-10 defined positions. A further alternative embodiment of the present invention is to have the assay reagent uniformly labelled with artificially enriched NMR active nuclei.

An assay reagent is a substance or compound that takes part in an assay, by being introduced as an initial reagent or by being formed in situ and perhaps transiently during the assay, or by being formed as a product of the assay. An assay is a test performed partly or wholly in vitro in which a physical or chemical change involving a biological species is observed. This change may have occurred both in vivo and in vitro. A biological species is one which is present in living systems or which is introduced into and is reactive with such systems. Preferred assay methods covered by this invention are related to biological macromolecules such as proteins (e.g. enzymes, receptors, DNA, and RNA binding proteins, carrier proteins), oligonucleotides (e.g. DNA and RNA probes, DNA and RNA consensus sequences), macrocyclic molecules (e.g. cyclodextrin) carbohydrate macromolecules and lipids.

Many assays involve a reaction in which a chemical bond is broken. According to another embodiment of the present invention, the assay reagent is an organic compound comprising one or more NMR active nuclei wherein these nuclei are associated with a bond which is broken during the course of the assay.

According to another embodiment of the present invention, the assay reagent contains two or more different types of NMR active nuclei, e.g. both $^{13}C$ and $^{15}N$. Each active nucleus produces a distinct NMR spectrum and when the assay method is performed its results in changes to the chemical and/or physical environment of the nucleus. The changes to the environment are mirrored by spectral changes, which can be monitored.

The degree of hyperpolarisation of the NMR active nucleus covered by this invention is in excess of 0.1%, more preferably I % and even more preferably at least 10% above the equilibrium population of the excited state.

Surprisingly, assay methods where even smaller enhancement is achieved may effectively be performed due to the shorter time needed for the total assay measurement. One important aspect of the present invention is thus an assay wherein the time required to give a defined signal-to-noise is considerably shortened by the use of this hyperpolarisation technique compared to known assay techniques without hyperpolarisation. The shortening effect is expressed as the improvement of signal-to-noise ratio per unit time, dB, Hz. This effect is preferably a factor of 10 or more, more preferably a factor of 25 or more and even more preferably a factor of 50 or more. In some embodiments, this effect is particularly a factor of 200 or more or even a factor of 1000 or more.

The assay can be carried out with the NMR active nucleus in the assay reagent already hyperpolarised. Alternatively, the assay may be carried out and the NMR active nucleus subsequently hyperpolarised prior, or at the same time, as the assay/assay reagent is analysed by NMR spectroscopy. Whilst the first arrangement enables real time studies of the assay to be carried out, this is often not necessary and, in these circumstances, the second method is very useful. As hyperpolarisation of the NMR active nucleus will sometimes be carried out at a low temperature, e.g. 20 K or less, the assay can be started and then effectively frozen by lowering the temperature. The assay/assay reagent is then hyperpolarised and analysed by NMR spectroscopy. By carrying out this process a number of times, either on the same assay or on parallel assays, a series of "snap-shots" of how the assay is proceeding may be obtained.

When hyperpolarisation is effected by exchange in solution phase, the hyperpolarising agent can be introduced as one batch, continuously or intermittently. Some conditions would lead to rapid disappearance of the hyperpolarisation. However, continuous or intermittent hyperpolarisation will give adequate signal intensity. Repeating the hyperpolarisation-acquisition sequence will also enhance the signal to noise ratio.

Agents, such as organic solvents, may in some situations be added to the assay, and/or to the NMR active nucleus if this is to be hyperpolarised prior to the assay, in order to prolong the life time of the hyperpolarised NMR active nucleus in the assay reagent, without interfering with the assay reagent and/or assay method.

Assays can be carried out by quantifying the appearance, or the continued presence, or the disappearance of spectral patterns. For example, on binding or hybridisation of an assay reagent the chemical shift of the signals derived from the NMR active nucleus in the assay reagent will change. The different relaxation times of the different NMR active nuclei need to be taken into account if the quantification measurement is to be accurate.

It will be apparent to those skilled in the art that some NMR active nuclei, also referred to herein as hyperpolarisable atoms, retain their hyperpolarisation for a longer period than others at a given set of physical parameters. Thus, the order in which steps (a) and (b) of the method are carried out may, to some extent, be determined by the choice of NMR active nucleus. Whilst there may be advantages in carrying out the hyperpolarisation of the assay reagent and then monitoring its NMR spectrum during the reaction, it is possible to "freeze" the reaction at any time. This may be achieved by reducing the temperature after the assay reagent has been added and then hyperpolarising the NMR active nucleus and comparing the spectra obtained with that of the assay reagent in a state where it has not undergone biological or chemical reaction(s).

As used herein, NMR active nuclei are those having non-zero nuclear spin and include $^1H$, $^{13}C$, $^{15}N$, $^{19}F$, $^{21}Si$, $^{31}P$ and deuterium. Of these, $^{13}C$ and $^{15}N$ are preferred and $^{13}C$ is particularly preferred. $^{13}C$ is present at a natural abundance (relative to $^{12}C$) of about 1%. Just as the labelling of organic compounds with radioactive $^{14}C$ is widely practised, so compounds, e.g. organic compounds can be labelled or enriched with $^{13}C$, either generally or at specific positions in the molecule. Preferably, the organic compounds for use in the assay according to this invention comprise an artificially-enriched abundance of $^{13}C$, either generally or at least in one specific position, at an abundance of at least 5%, suitably at least 10%, more suitably at least 50%, preferably at least 75%, more preferably at least 90% and ideally at approaching 100%.

The present invention also covers the use of compounds comprising an artificially-enriched abundance of $^{15}N$ of at least 1%, suitably at least 5%, more suitably at least 10%, preferably at least 50% and more preferably at least 75% or more, and ideally at approaching 100%.

For assay reagents comprising $^{29}$Si the preferred level of artificially enriched abundance is at least 10% and more preferred at a level of 50% or more, even more preferably at least 75% or more and ideally at approaching 100%.

For achieving as long $T_1$ as possible, the enriched compounds in some methods covered by the invention are preferably those in which the NMR active nucleus is surrounded by a double bond or one or more non-MR active nuclei such as O, S and/or C. In some cases, nearby protons to the NMR active nucleus may be substituted by deuterium.

In one embodiment of the invention, step c) is performed by examining the assay reagent using both NMR spectroscopy to obtain spectral data from one or more discrete physical locations and repeating the examination at least once so as to obtain quantitative information about kinetic or time-dependant alteration in chemistry, environment or structure of the assay reagent.

Assays envisaged according to this invention include for example, competition assays (e.g. receptor-ligand antagonism, enzyme-substrate inhibitors, protein-protein interaction inhibitors), binding assays (e.g. receptor-ligand agonism, enzyme-substrate reactions, protein-protein interactions), immunoassays (e.g. for specific analytes), hybridisation assays (e.g. nuclease assays, mutation analysis, mRNA and DNA detection), tests involving cells, organs and/or whole organisms. Thus, the invention covers binding studies performed on tissue sections, cultured cells, cellular metabolites, micro-organisms and macro-organisms. Preferred examples are discussed in the following paragraphs. Labelling with an NMR active nucleus where each molecule may be labelled at one or more chemical positions, will allow unique NMR assignments of e.g. starting material, intermediates and products of a biological reaction. Thus dual, triple etc labelling experiments can be carried out and 'stop-flow' measurements made with identical chemical species. For example, theoretically, all the six carbon atoms in glucose could be individually or collectively replaced by $^{13}$C, so that one to six of the carbon atoms are $^{13}$C which can be hyperpolarised. Each hyperpolarised $^{13}$C will give rise to a chemical shift, which will be specific to that individual carbon and different to other $^{13}$C positions in the molecule, i.e. C-1 will be different from C-2, etc.

A non-exclusive list of the types of molecules into which NMR active nuclei may be incorporated includes:

(i) Amino Acids

Amino acids contain carbon, nitrogen and hydrogen and therefore any amino acid can be labelled at a single or multiple positions with one or more different NMR-active nuclei.

(ii) Lipophilic Compounds

These would contain fatty acids, phospholipids, glycerol, cholesterol and its esters, sphingosine and its esters. These contain carbon, hydrogen and in some cases nitrogen and/or phosphorus and can be labelled at a single or multiple positions with one or more different NMR-active nuclei.

(iii) Vitamins

These include the water-soluble and fat-soluble categories of essential nutrients. These contain carbon, hydrogen and in some cases nitrogen and/or phosphorus and can be labelled at a single or multiple positions with one or more different NMR active nuclei.

(iv) Nucleic Acids Etc

DNA contains the bases adenine, cytosine, guanine and thymine and their nucleosides and nucleotides. RNA contains the bases adenine, guanine, cytosine and uracil and their nucleosides and nucleotides. These contain carbon, hydrogen, nitrogen and in some cases phosphorus and can be labelled at a single or multiple positions with one or more different NMR-active nuclei.

In one preferred embodiment of the invention the hyperpolarisation transfer is achieved by using a hyperpolarised noble gas, or a mixture of such gases, to effect nuclear polarisation of an assay reagent comprising at least one NMR active nucleus other than the noble gas.

When the hyperpolarisation of the assay reagent is achieved by an artificially enriched hyperpolarised noble gas, the hyperpolarised noble gas is preferably $^3$He or $^{129}$Xe. Such isotopically enriched gases are now commercially available at high isotope purity and can be polarised to a high degree of hyperpolarisation. The hyperpolarised gas may, if desired, be stored for extended periods of time in the polarised state, by keeping the gas at very low temperatures, especially in a frozen form.

A hyperpolarised noble gas may be used in step b) of the present invention to effect nuclear polarisation of an assay reagent comprising at least one NMR active nucleus other than the noble gas. The hyperpolarised gas may be in the gas phase, condensed or may alternatively be liquid e.g. by being dissolved or emulsified in a lipophilic solvent such as a lipid or a fluorocarbon solvent, or in a suspension or a solid e.g. by being adsorbed or frozen on to a solid surface. In some cases, liposomes or microbubbles may encapsulate the hyperpolarised noble gas.

The assay reagent may be solid, semi-solid or fluid. A hyperpolarised gas may be bubbled into a fluid assay system. Alternatively, a hyperpolarised gas solution may be mixed with a fluid assay. The hyperpolarised gas may be cooled and/or maintained in a magnetic field to preserve the hyperpolarisation. Similarly the resulting assay reagent comprising at least one polarised NMR active nucleus may preferably be cooled and/or maintained in a magnetic field in order to preserve the polarisation and/or facilitate polarisation transfer.

One advantage with hyperpolarisation transfer by $^3$He or $^{129}$Xe is that these gases are essentially chemically inert and will not adversely affect the assay reagent or the assay. In addition, as in gaseous form, $^3$He and/or $^{129}$Xe are easily separated from the assay medium, permitting facile repeat studies.

In one embodiment, a flow of hyperpolarised gas in the liquid state at elevated pressure and/or low temperature is passed through a column of the assay reagent. The gas may be pumped off and the process repeated until a suitable level of polarisation is achieved. Alternatively, a hyperpolarised gas is frozen/crystallised on the solid/frozen surface of the solid assay reagent. This compound may preferably have been prepared with as large a surface area as possible, e.g. as a finely divided powder.

In some cases, it is desirable to remove part of or substantially the whole of the hyperpolarisable gas from the assay reagent/system as rapidly as possible. If desired, the gas may be reused which may be important due to the expense of isotopically-enriched noble gases. Many physical and chemical separation or extraction techniques known in the art may be employed to effect rapid and efficient separation of the hyperpolarised gas and the assay system.

In one embodiment of the invention when performed with the assay reagent in the solid phase, it is especially important that the content of $^{131}$Xe should be as low as possible. The preferred content of $^{131}$Xe is thus below 0.5% of the total Xe content, and more preferably below 0.05%.

In a further aspect, the present invention provides a method for optimising the polarisation enhancement factor when the assay reagent is hyperpolarised by a noble gas in solution. Thus the enhancement of the target nuclear spin can be optimised by slowing the dynamics of the molecules (atoms) in the solution. The dynamics can be slowed down, e.g. by increasing the viscosity of the solvent. The polarisation enhancement factor may also depend on the concentration of the noble gas in the solution and the enhancement factor may be optimised further by adjusting the pressure and temperature.

The relaxation mechanisms and also the relaxation of the target nucleus are partly functions of the viscosity of the solvent. For a specific system of interest we may choose the optimal viscosity of the medium that will lead to the maximal polarisation enhancement factor of the target nucleus. The viscosity is determined by choice of solvent and temperature. Preferably, the viscosity should be at least 1000 mPs, more preferably at least 10000 mPs and especially preferably at least 100000 mPs.

In one embodiment of the invention, when the polarisation transfer occurs in solution, the pressure of xenon is as high as possible, preferably higher than $5 \times 10^5$ N/m$^2$ (5 bar), more preferably higher than $5 \times 10^6$ N/m$^2$ (50 bar), even more preferably higher than $1 \times 10^7$ N/m$^2$ (100 bar) and particularly higher than $2 \times 10^7$ N/m$^2$ (200 bar). However, the pressure must never be so high so that the biological molecule will be totally or partly adversely effected.

It is preferred that the solvent comprises as few atoms which possess magnetic moment as possible and is as low magnetogyric ratio as possible. The transfer of polarisation in a highly viscous medium maybe followed by solution spectroscopy under high-viscosity conditions (broad lines).

Alternatively, the viscosity may be lowered prior to spectroscopy, either by a change in temperature or by a change in the chemical composition of the solvent. If the high-viscosity medium is formed by a pH-sensitive gel-forming agent, then the viscosity might be lowered e.g. by a change in pH. Changes of temperature, ion-strength as well as the use of specific additives may also be considered.

In a further embodiment, the present invention provides a method wherein the hyperpolarisation transfer is effected by use of a very high field and with very low temperature (Brute force). The magnetic field strength used should be as high as possible, suitably higher than 1T, preferably higher than 5T, more preferably 15T or more and especially preferably 20T or more. The temperature should be very low e.g. 4.2K or less, preferably 1.5K or less, more preferably 1.0K or less, especially preferably 100 mK or less.

U.S. Pat. No. 5,479,925 discloses a method for generating MR angiograms in which a contrast agent is passed through a small, high field polarising magnet in vitro in order to generate a high longitudinal magnetisation in the agent prior to its administration to the subject. However, there is no mention of the use of an enriched NMR active nucleus. When this Brute force method is used, and thermodynamic equilibrium is attained, all nuclei in the assay reagent will be highly polarised relative to room temperature and to normal magnetic fields used in MRI.

A major practical problem when using this technique is the time required for the thermal equilibrium to occur. However, the Brute force embodiment may be modified in order to solve this problem as described below.

It is possible to use a technique of low-field matching to increase the relaxation rate and the degree of polarisation of the nuclear spins in solids at low temperature. This has the additional advantage that equipment used in the Brute force polariser does not need to possess any radio frequency electronics.

A way of speeding up the polarisation of the NMR active nuclei, at least for $^{13}$C and $^{15}$N and at the same time obtaining a better polarisation is to use cross-polarisation from the quickly relaxing proton to the slowly relaxing carbon, a method routinely used in solid-state NMR spectroscopy. The situation may be further improved by utilising the procedure of spin locking under Hartman-Hahn conditions. However, radiofrequency electronics are required and furthermore the homogeneity of the magnetic field must be high enough to allow precise pulse angles. A simplified method to allow for thermal contact between the protons and the NMR active nucleus (e.g. $^{13}$C or $^{15}$N) is to remove the assay from the magnet for a fraction of a second and repeat this procedure after the protons have repolarised, successively building up the polarisation until the spin-temperature of the two nuclei become the same.

A further improvement of the Brute force embodiment of this invention is to optionally expose the assay system to a relaxation shortening effect in order to attain thermodynamic equilibrium at said low temperature. The relaxation shortening effect may be provided by exposure to field cycling to a field allowing cross polarisation, gradually increasing the magnetic field at such a rate that the increase in polarisation of the assay reagent is maximised. This effect may also be achieved by adding magnetic material to the assay reagent during the period when the assay reagent is exposed to low temperature.

In a further embodiment, the present invention provides a method for the polarisation transfer using the DNP method effected by a DNP agent, to effect nuclear polarisation of an assay reagent comprising at least one NMR active nucleus. In the solid phase, there are two aspects of DNP, namely "the solid effect" and the thermal mixing.

Most known paramagnetic compounds may be used as a "DNP agent" in this embodiment of the invention, e.g. transition metals such as chromium ions or organic free radicals such as nitroxide radicals and trityl radicals (WO 98/58272) Where the DNP agent is a paramagnetic free radical, the radical may be conveniently prepared in situ from a stable radical precursor by a radical-generating step shortly before the polarisation, or alternatively by the use of ionising radiation. Energy, normally in the form of microwave radiation, is provided in the process which will initially excite the paramagnetic species. Upon decay to the ground state, there is a transfer of polarisation to an NMR active nucleus of the target material. The method maybe conveniently carried out by using a first magnet for providing the polarising magnetic field and a second magnet for providing the primary field for MR spectroscopy/imaging.

In some cases, the radical will be non-reusable and may conveniently be discarded after use. Many physical and chemical separation or extraction techniques are known in the art, which may be used if it is desirable to remove the DNP agent from the assay system in a rapid and/or efficient separation step. Magnetic properties may e.g. be used to achieve the separation. It is particularly preferred to use a heterogeneous system, e.g. a two-phase liquid, a solid in liquid suspension or a high surface area solid substrate within a liquid. For any heterogeneous system, separation may be achieved by e.g. filtration, decanting, chromatographic or centrifugal methods.

In a further embodiment, the present invention provides a method wherein the polarisation transfer is achieved by exposing the assay reagent to para hydrogen-enriched hydrogen gas in the presence of a suitable catalyst. The assay reagents suitable for use are prepared from precursors which are able to be hydrogenated and which will therefore typically possess one or more unsaturated bonds, e.g. double or triple carbon-carbon bonds.

Hydrogen molecules exist in two different forms, para hydrogen (p-H2) where the nuclear spins are anti parallel and out of phase (singlet state) and ortho hydrogen (o-H2) where the spins are parallel or anti parallel and in phase (triplet state). At room temperature, the two forms exist in equilibrium with a 1:3 ratio of para:ortho hydrogen. However, preparation of para hydrogen enriched hydrogen can be carried out at low temperature, 160K or less, in the presence of a catalyst. The para hydrogen formed may be stored for long periods, preferably at low temperature, e.g. 18-20K. Alternatively it may be stored in pressurized gas form in containers which have an inner surface which is non-magnetic and non-paramagnetic.

When the p-H2 molecule is transferred to the precursors of the assay reagent (by means of catalytic hydrogenation with e.g. $(PPh_3)_3RhCl$), the proton spins remain anti parallel and begin to relax to thermal equilibrium with the normal constant T I of the hydrogen in the assay molecule. However, during relaxation some of the polarisation may be transferred to neighbouring nuclei by pulse sequence (Progress in Nuclear Spectroscopy, 31, (1997), 293-315), low field cycling or other types of coupling. The presence of the NMR active nucleus as e.g. $^{13}C$ (and $^{15}N$ etc) with a suitable substitution pattern close to the relaxing hydrogen may lead to the polarisation being trapped in the slowly relaxing $^{13}C$ (or $^{15}N$ etc) resulting in a high enhancement factor.

A further hyperpolarisation transfer embodiment of this invention is the spin refrigeration method. This method covers spin polarisation of a solid assay by spin refrigeration polarisation. The assay is doped with or intimately mixed with a suitable paramagnetic material such as $Ni^{2+}$ lanthanide and actinide ions in crystal form with a symmetry axis of order three or more. The instrumentation is simpler than that required for DNP with no need for a uniform magnetic field. The process is carried out by physically rotating the sample around an axis perpendicular to the direction of the magnetic field. The prerequisite for this to work is that the paramagnetic species has a highly anisotropic g-factor.

Hybridisation assays are very widely used for sequencing and for detection of point or deletion mutations in nucleic acids. When a conventionally labelled polynucleotide probe is hybridised with a polynucleotide target, analysis of the melting temperature or other property of the hybrid can give some limited information about the nucleotide sequence of the target.

The present invention can give the same information about the target compared to any previously known NMR methods available, but with the advantage of increased sensitivity. A polarised NMR active nucleus generates an NMR spectrum which is dependent on its environment, i.e. the atoms surrounding the NMR active nucleus, both intramolecular (atoms within the same molecules as the NMR active nucleus) and intermolecular (atoms in the other molecules nearby the NMR active nucleus). The environment thus extends beyond the labelled molecule itself to other molecules in the immediate vicinity. Thus for example, a nucleotide labelled with polarised NMR active nucleus, e.g. $^{13}C$ and/or $^{15}N$, when incorporated into a single stranded polynucleotide chain, can give information about two or more adjacent nucleotide residues in the chain. When that labelled polynucleotide probe is hybridised with a polynucleotide target, NMR spectroscopic analysis of the NMR $^{13}C$ label can give information about the complementary nucleotide residue in the target.

In one embodiment of the present invention, comparative and/or parallel testing is performed to maximise the information available from the NMR measurements.

Biological macromolecules such as nucleosides or nucleotides or nucleotide analogues can readily be enriched with a NMR active nucleus, e.g. $^{13}C$ and/or $^{15}N$ at one or several specified points in the molecule. Polarisation of the NMR active nucleus, e.g. $^{13}C$, preferably by contact with a hyperpolarised noble gas, may be effected either before, during or after incorporation of the monomer into a polynucleotide; and before, during or after hybridisation of that polynucleotide with a complementary strand.

FIG. 1 demonstrates a hybridisation assay in which the use of an oligonucleotide or polynucleotide is used to detect the presence of single nucleotide polymorphisms (SNPs) in a gene, or fragment of a gene. An oligonucleotide or polynucleotide probe is prepared in which one or more of the atoms has been replaced by a hyperpolarisable isotope, e.g. $^{13}C$, $^{15}N$ or $^{1}H$. This probe is then hybridised to the gene or the gene fragment. The probe will be "targeted" to information-rich parts of the gene and may be selected so that the probe binds only to that part of the DNA containing a specific mutation, or, potentially, more than one mutation. If desired, a set of probes, each probe containing a hyperpolarisable isotope, can be added to a gene or gene fragment, each probe being targeted to a different part of the gene/gene fragment. As each probe will have a characteristic chemical shift by NMR spectroscopy, the spectrum of the mixture of the probes with the target can be taken and resolved to indicate which probes have bound and which have not.

The probe may be polarised before, during, or after hybridisation and a determination carried out by NMR of whether a shift has occurred in the signal obtained from the hyperpolarised isotopic atom(s). If a shift has. occurred, then the probe is (by inference) in a different chemical environment indicating hybridisation. Clearly information can be obtained from both positive and negative results, e.g. a probe could be constructed from the "natural" gene, a naturally occurring DNA sequence, and if results indicate that this has failed to bind, probes could be tested containing anticipated mutations. This technique facilitates itself to use of an array-type format in which a number of hyperpolarisable probes are used in the assay which each vary by one nucleotide. The identity of the SNP can be determined by the hybridisation pattern of the probes to the gene/gene fragment.

As mentioned earlier, many assays involve a reaction in which a chemical bond is broken. According to one embodiment of the present invention, the assay reagent is an organic compound comprising one or more NMR active nuclei associated with a bond which is broken during the course of the assay. In the case of a single NMR active nucleus, this is located preferably at the actual site of the breaking of the chemical bond such that the change in local environment of the active nucleus subsequent to the bond breaking will give rise to a significant change in the spectrum of the NMR active nucleus. The NMR spectra of two or more active nuclei will be different, depending on whether they are present within the same molecule or in different molecules. When two or more NMR active nuclei are in an appropriate proximity to one another they are said to be spin coupled. This gives rise to a distinct NMR spectrum which can be monitored. It is therefore possible to analyse by NMR spectroscopy the rate and extent of the bond breaking by the disruption of the spin coupling. In this and other assays, the assay reagent may be analysed repeatedly by NMR spectroscopy at known time intervals so as to generate information about a change over time of the assay reagent.

Figure 2:
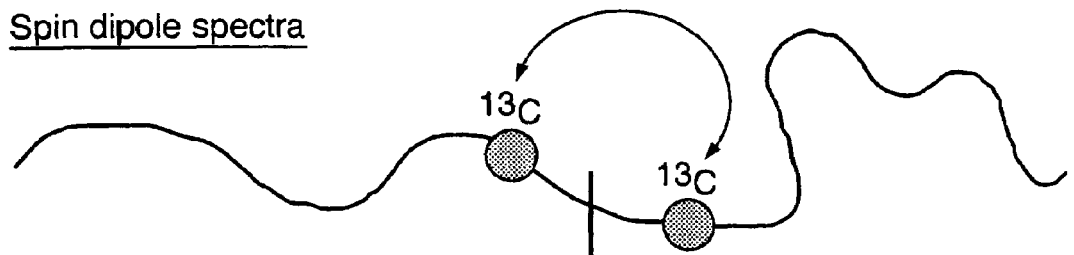
FIG. 2 is a schematic representation of a peptide containing two 13C isotopes before (top) and after (bottom) cleavage between said two 13C isotopes.

FIG. 2 demonstrates a proteolysis assay. The starting substrate for the reaction contains two hyperpolarisable isotopes, in this case $^{13}C$, which are sufficiently close together, either by virtue of being reasonably adjacent in the chain of amino acids comprising the molecule, or by the 3-dimensional conformation of the molecule held in a "conformational lock". In these situations, NMR spectra J coupling (scalar coupling) of the signal occurs and the NMR spectra of the molecule is recorded.

The molecule is then brought into contact with an enzyme capable of altering the chemical composition of the substrate. If cleavage occurs between the amino acids containing the hyperpolarisable isotopic atoms, then the J coupling and the chemical shift values change which will be observed by NMR spectoscopy and/or NMR imaging. Two new spectra will appear, one for each of the individual cleavage products. If there is no cleavage, the original spectrum remains.

A similar assay can be carried out where the starting substrate is a chain of nucleotides and the cleavage enzyme an endonuclease.

In another aspect of the invention, an assay reagent may be administered to a macro-organism, e.g. a human or animal, and NMR spectroscopic analysis performed of blood, excreta, e.g. urine, faeces or breath, or samples of the macro-organism.

In yet another aspect of the invention, an assay reagent may be used in binding studies on bacteria or other eukaryotic or prokaryotic micro-organisms or cultured cells.

Assays according to one embodiment of this invention may conveniently be carried out in multiwell plates. An assay reagent in each well may e.g. be hyperpolarised by contact with a hyperpolarised noble gas, prior to addition of other assay reagents. Alternatively, an assay reagent in bulk may be hyperpolarised with a hyperpolarised noble gas prior to being dispensed into individual wells of a multiwell plate. In many cases, assays can be performed in a homogenous mode, that is to say without the need for a separation step to remove one fraction of the labelled reagent.

In addition, in cases where the spectra of the $^{13}C$ labelled assay components are distinct from one another, more than one assay may be performed and simultaneously monitored in a single well or spot of a multi-assay array. This would allow multiplexing of several related or unrelated assays in parallel within a single well or spot in a multi-assay array which is either ordered or random. In addition the technique may be applied to aerosol droplets where no well, container or surface is used to contain the assay and to analysis of samples in flow-through devices.

Figure 3:
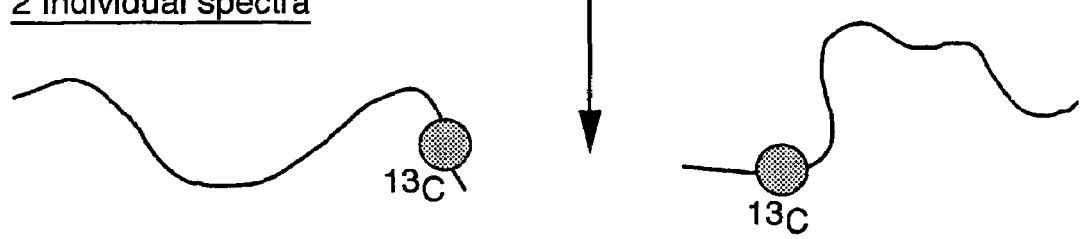
FIG. 3 is a schematic representation of a cell wherein material comprising 13C is shown extracellularly (#1) and then transferring intracellularly (#2), subcellularly (#3), or becoming bound to the cell surface (#4).

FIG. 3 illustrates how the incorporation of a material (for example an amino acid) into a cell can be measured. The material incorporates a hyperpolarisable isotopic atom, in this case $^{13}C$. Its NMR spectrum in a hyperpolarised state in the media used for the experiment is recorded. If the material crosses the cell membrane then the environment in which the material finds itself will change and this will affect the NMR chemical shift of the material. The precise chemical shift will depend on the environment of the material within the cell, for example it may be possible to identify whether it has crossed into the cell nucleus. Alternatively, the material may be bound to the surface of the cell, again a different spectrum will result. In addition, metabolites that contain ahyperpolarisable isotopic atom maybe detected either inside the cell or after they are excreted from this. The spectra obtainable on these metabolites can be used for their identification and/or to give information on their structure.

In one embodiment of the present invention, the assay is performed at a relatively cold temperature. However, in some situations the assay is carried out at room temperature.

It is important that the probes, vials, coils etc are coated or made of materials which do not induce loss of polarisation, such as para-magnetic nuclei. Preferred such materials are e.g. plastic, aluminium, Teflon and glass (with low iron content) materials. A further embodiment of the method according to the invention is thus the use of materials such as aluminium, plastic, glass and/or Teflon for the wells, vials, containers and any coils. A metal may also be used coated with a non-para magnetic oxide layers (e.g. Ti, Mg or Ag).

In one preferred embodiment of the invention, the assay is carried out in an NMR tube, with a gas-tight seal, permitting the addition (and/or removal) of a hyperpolarised gas to (and/or from) the assay reagent.

A variety of NMR spectroscopy and/or NMR imaging manipulation methods may be used, e.g. magic angle spinning and pulse sequence like WAHUHA or MLEV-8 to obtain high resolution spectrum when the assay reagent is a solid or semi-solid state.

A further embodiment of the present invention is an in vitro kit for carrying out. the assay method as defined. The kit comprises a well, vial or any other suitable container comprising one or more assay reagents optionally together with additives wherein the hyperpolarisation transfer occurs. One embodiment of the invention concerns an in vitro kit where the NMR analysis of step (c) of claim 1 is carried out in the same well, vial or container as the polarisation transfer is carried out.

The invention is illustrated with reference to the following non-limiting example. Modifications of the method according to this example include the addition of the noble gas directly into the spectrometer and the use of different pulse techniques.

EXAMPLE 1

Polarisation transfer from hyperpolarised $^{129}Xe$ to the singly labelled peptide AcYRARV(F,$^{13}C$-amide)FVPAAK-NH$_2$.

Hyperpolarized $^{129}Xe$ was generated by optical pumping as described by B. Driehuys et al., Appl.Phys.Lett. 69 (12), 1996. The isotopic composition of the gas was 80% $^{129}Xe$ and 0.25% $^{131}Xe$ (the rest non-magnetic isotopes of Xe). The degree of polarization was estimated to be 10%±3.

The freeze-dried peptide (3.4 mg) was placed in an ordinary 5 min thin-walled NMR-tube. The glass tube was connected to the outlet of the polarizer by means of 60 cm of plastic tubing. The tube was evacuated and then filled with nitrogen four times.

The hyperpolarized gas was generated and collected on a cold finger at liquid nitrogen temperature in a holding field of 200 mT over a period of 15 minutes which is estimated to give a volume of 50 ml of Xenon at NTP. A narrow Dewar vessel with liquid nitrogen was placed in a magnet with a field strength of 0.3 T. The collected xenon was thawed and gradually refrozen on the peptide from the bottom and up by gradually lowering the tube into the liquid nitrogen bath. The system was then filled with helium to one atmosphere. The sample, with the plastic tubing still connected but open to the surroundings, in the Dewar in the 0.3 T magnet with the poles in horizontal configuration was then moved into the stray-field of the 7 T magnet (vertical polarity) of an NMR-spectrometer. The sample was then rapidly transferred to the spectrometer and was in the process subjected to a minimum magnetic field of 0.3 mT.

A $^{13}$C spectrum was recorded with a spectral window of 100 kHz and a broad $^{13}$C signal was obtained. The sample was then left to polarize in the magnet and a background signal was recorded overnight, and care was taken to allow for full relaxation between the pulses.

The enhancement was measured to 6±1 times the thermodynamic equilibrium at 7 T and 291 K.

The time from the beginning of freezing the xenon in the NMR tube to the acquisition of the spectrum was 5 minutes.

What is claimed is:

1. A liquid state in vitro assay method to detect a physical or chemical change involving a chemical or biological species which comprises the steps of:
   a) performing an assay on a biological species using an assay reagent containing at least one NMR active nucleus, said assay reagent being one of i) introduced as an initial reagent, ii) formed in situ during the assay, and iii) formed as a product of the assay, and
   b) hyperpolarising at least one NMR active nucleus of the assay reagent by dynamic nuclear polarization comprising mixing the assay reagent with a paramagnetic species (DNP agent) and/or a free radical generator or other particles having associated free electrons; wherein the degree of hyperpolarisation of the NMR active nucleus is in excess of 0.1%, and wherein steps (a) and (b) are performed simultaneously or sequentially in either order, and
   c) analysing the NMR active nucleus of the assay reagent and/or the assay by NMR for a physical or chemical change in said biological species that is independent of the interaction of the biological species with the NMR active nucleus; and
   d) optionally using the NMR data obtained in step c) to generate further assay result(s)
   wherein the NMR active nucleus comprises one of $^{15}$N, $^{19}$F, $^{31}$P, $^{1}$H, $^{29}$Si and $^{13}$C.

2. The method of claim 1, wherein the NMR active nucleus is $^{15}$N or $^{13}$C.

3. The method of claim 1, wherein the assay reagent is a compound which contains an artificially enriched abundance of an NMR active nucleus.

4. The method of claim 3, wherein the assay reagent contains an artificially enriched abundance of the NMR active nucleus in up to 10 defined positions.

5. The method of claim 3, wherein the assay reagent contains an artificially-enriched abundance of the NMR active nucleus in one specific position.

6. The method of claim 1, wherein the assay reagent is an organic compound comprising an NMR active nucleus located at the site of a chemical bond which is broken during the course of the assay.

7. The method of claim 1, wherein the assay reagent is analysed repeatedly in step c) at known time intervals so as to generate information about a change with time of the assay reagent.

8. The method of claim 1, wherein the assay reagent is a nucleotide, nucleotide analogue, polynucleotide, amino acid analogue, polypeptide or protein.

9. The method of claim 1, wherein the assay is a nucleic acid hybridisation assay.

10. The method of claim 1, wherein the assay is a binding assay.

11. The method of claim 1, wherein the assay reagent is a compound specifically labelled with at least one NMR active nucleus and the assay reagent is administered to a microorganism, macro-organism or cultured cells, and wherein cellular metabolites or an excretion product of the assay reagent are hyperpolarised and analysed by nuclear magnetic resonance spectroscopy, nuclear magnetic resonance imaging or both.

12. The method of claim 1, wherein the assay is a binding study performed using micro-organisms or cultured cells.

13. The method of claim 1 wherein said step (b) is repeated to enhance the signal-to-noise ratio.

14. The method of claim 1 wherein the method exhibits a shortening effect as expressed by the improvement of signal-to-noise per unit time by a factor of 10 or more compared to said method being carried out without hyperpolarisation.

15. The method of claim 1 where the hyperpolarisation of the NMR active nucleus of the assay reagent is carried out by polarisation transfer at a temperature of 4.2 K or less in the presence of a magnetic field of at least 1 T.

16. The method of claim 1, wherein more than one assay is multiplexed and monitored by NMR spectroscopy and/or NMR imaging.

17. The method of claim 1 wherein the assay is performed in a multiwell or multispot assay array.

18. The method of claim 1 wherein step c) is performed by examining the assay reagent using both NMR spectroscopy to obtain more than one spectrum, and magnetic resonance imaging to obtain one or more discrete spectral location, and repeating the examination at least once so as to obtain quantitative information about kinetic or time-dependant alteration in chemistry, environment or structure of the assay reagent.

19. The method of claim 1, wherein step c) is performed in an aerosol where no well, surface or container is used to contain the assay reagent, or wherein step c) is performed in a flow-through device applied to aerosol droplets.

20. The method of claim 1 wherein the assay reagent is an organic compound comprising two or more NMR active nuclei associated with a chemical bond which is broken during the course of the assay such that when the bond is intact, the said NMR active nuclei are spin coupled and when the bond is broken the spin coupling is disrupted.

* * * * *